(12) United States Patent
Anderson et al.

(10) Patent No.: US 7,505,808 B2
(45) Date of Patent: Mar. 17, 2009

(54) CATHETER TRACKING WITH PHASE INFORMATION

(75) Inventors: Kevan J. T. Anderson, Toronto (CA); Graham A. Wright, Toronto (CA)

(73) Assignee: Sunnybrook Health Sciences Centre, Toronto, ON (CA)

( * ) Notice: Subject to any disclaimer, the term of this patent is extended or adjusted under 35 U.S.C. 154(b) by 558 days.

(21) Appl. No.: 11/115,416

(22) Filed: Apr. 27, 2005

(65) Prior Publication Data
US 2005/0245814 A1 Nov. 3, 2005

Related U.S. Application Data

(60) Provisional application No. 60/565,845, filed on Apr. 28, 2004.

(51) Int. Cl.
*A61B 5/055* (2006.01)
(52) U.S. Cl. ...................................... 600/411; 600/424
(58) Field of Classification Search ................. 600/407, 600/410, 424, 433–435, 429, 411; 324/307, 324/309, 318, 322; 702/150–154
See application file for complete search history.

(56) References Cited

U.S. PATENT DOCUMENTS

| | | | | |
|---|---|---|---|---|
| 5,211,165 | A * | 5/1993 | Dumoulin et al. | 600/410 |
| 5,271,400 | A * | 12/1993 | Dumoulin et al. | 600/410 |
| 5,377,678 | A * | 1/1995 | Dumoulin et al. | 600/424 |
| 5,868,674 | A * | 2/1999 | Glowinski et al. | 600/410 |
| 6,427,079 | B1 * | 7/2002 | Schneider et al. | 600/424 |
| 6,516,213 | B1 * | 2/2003 | Nevo | 600/424 |

OTHER PUBLICATIONS

Axleander J. Dick et al., Magnetic Resonance Fluoroscopy Allows Targeted Delivery of Mesenchymal Stem Cells to Infarct Borders in Swine, http://www.circulationaha.org, Dec. 9, 2003; pp. 2899-2904.
Jorg Barkhausen et al., Detection of Atherosclerotic Plaque with Gadofluorine-Enhanced Magnetic Resonance Imaging, http://www.circulationaha.org, Aug. 5, 2003, pp. 605-609.

(Continued)

*Primary Examiner*—Ruth S Smith
*Assistant Examiner*—Peter Luong
(74) *Attorney, Agent, or Firm*—Lynn C. Schumacher; Hill & Schumacher

(57) ABSTRACT

A method for determining the position and/or orientation of a catheter or other interventional access device or surgical probe using phase patterns in a magnetic resonance (MR) signal. In the method of the invention, global two-dimensional correlations are used to identify the phase pattern around individual microcoils, which is unique for each microcoil's position and orientation. In one embodiment the position and orientation of a catheter tip can be reliably tracked using low resolution MR scans clinically useful for real-time interventional MRI applications. In a further embodiment, the invention provides real-time computer control to track the position of endovascular devices and interventional treatment systems, including surgical tools and tissue manipulators, devices for in vivo delivery of drugs, angioplasty devices, biopsy and sampling devices, devices for delivery of RF, thermal, microwave or laser energy or ionizing radiation, and internal illumination and imaging devices, such as catheters, endoscopes, laparoscopes, and related instruments.

32 Claims, 8 Drawing Sheets

Step 1
Obtain axial phase pattern with no slice selection.
Determine:
- Position in x-y plane
- Rotation angle θ about z-axis Step 2
Prescribe oblique scan plane through center of coil

OTHER PUBLICATIONS

Jolanda J. Wentzel et al., Vascular MRI in the Diagnosis and Therapy of the High Risk Atherosclerotic Plaque, Journal of Interventional Cardiology, vol. 16, No. 2, 2003 pp. 129-142.

Arndt Glowinski et al., Catheter Visualization Using Locally Induced, Actively Controlled Field Inhomogeneties, MRM 38:253-258 (1997) From the Clinic for Diagnostic Radiology, University of Technology Aachen, Germany.

CJG Bakker et al, Dedicated Catheters for Susceptibility—Based MR Visualization, Department of Radiology, University Hospital Utrecht, The Netherlands, pp. 900-901.

C.L. Dumoulin et al., Real-Time Position Monitoring of Invasive Devices Using Magnetic Resonance[1], MRM 29:411-415 (1993).

Daniel R. Elgort et al., Real-Time Catheter Tracking and Adaptive Imaging, Journal of Magnetic Resonance Imaging 18:621-626 (2003).

J.M. Santos et al., Multi-Coil Real-Time Inverventional System, Proc. Intl. Soc. Mag. Reson. Med. 11 (2003) pp. 1197.

Marc E. Miquel et al., Visualization and Tracking of an Inflatable Balloon Catheter Using SSFP in a Flow Phantom and in the Heart and Great Vessels of Patients, Magnetic Resonance in Medicine 51:988-955 (2004).

Sebastian Kozerke et al., Catheter Tracking and Visualization Using [19]F Nuclear Magnetic Resonance, Magnetic Resonance in Medicine 52:693-697 (2004).

Jean-Michel Serfaty et al, Toward MRI-Guided Coronary Catheterization: Visualization of Guiding Catheters, Guidewires, and Anatomy in Real Time, Journal of Magnetic Resonance Imaging 12:590-594 (2000).

Robert J. Lederman et al., Catheter-Based Endomyocardial Injection with Real-Time Magnetic Resonance Imaging, http://www.circulationaha.org, Mar. 19, 2002, pp. 1282-1284.

P.V. Karmarkar et al., MR-Trackable Intramyocardial Injection Catheter, Magnetic Resonance in Medicine 51:1163-1172 (2004).

Michael Bock et al , MR-Guided Intravascular Procedures: Real-TIme Parameter Control and Automated Slice Positioning With Active Tracking Coils, Journal of Magnetic Resonance Imaging 19:580-589 (2004).

Chris Flask et al., A Method for Fast 3D Tracking Using Tuned Fiducial Markers and a Limited Projection Reconstruction FISP (LPR-FISP) Sequence, Journal of Magnetic Resonance Imaging 14:617-627 (2001).

Claudia M. Hillenbrand et al., Active Device Tracking and High-Resolution Intravascular MRI Using a Novel Catheter-Based, Opposed-Solenoid Phased Array Coil, Magnetic Resonance in Medicine 51:668-675 (2004).

Sven Zuehlsdorff et al., MR Coil Design for Simulataneous Tip Tracking and Curvature Delineation of a Catheter, Magnetic Resonance in Medice 52:214-218 (2004).

Steffen Weiss et al., In Vivo Safe Catheter Visualization and Slice Tracking Using an Optically Detunable Resonant Marker, Magnetic Resonance in Medicing 52:860-868 (2004).

C.M. Hillenbrand et al., A Catheter Based, Opposed Solenoid Phased Array Coil for Actice Device Tracking and High Resolution Intravascular MRI, Proc. Intl. Soc. Mag. Reson. Med. 11 (2003) pp. 1186.

\* cited by examiner

CATHETER TRACKING WITH PHASE INFORMATION

CROSS REFERENCE TO RELATED U.S PATENT APPLICATIONS

This patent application claims priority from U.S. provisional patent application Ser. No. 60/565,845 filed on Apr. 28, 2004 entitled CATHETER TRACKING WITH PHASE INFORMATION.

FIELD OF THE INVENTION

The present invention relates to a method for determining the position and/or orientation of a catheter or other interventional access device or surgical probe using phase patterns in a magnetic resonance (MR) signal.

BACKGROUND OF THE INVENTION

Catheters and other endovascular access tools have long been used in the art as medical devices to advance therapeutic agents to an anatomic point of interest for examination, diagnosis, and intervention. Accurate positioning of such interventional devices requires monitoring to ensure that the device is being advanced through the correct structures without causing injury, failing mechanically, and for other reasons known to one skilled in the art.

Methods existing in the art for such monitoring include X-ray visualization, as well as MRI tracking of any component of the device designed to be visible on MRI. Many conventional vascular interventional procedures use X-ray imaging technology in which catheters or other probes are inserted into a vein or artery and navigated to specific locations for diagnostic and therapeutic procedures. For example, over 3,000 trans-septal procedures are performed each year in the United States for left sided radio-frequency ablation therapy and mitral valvoplasty procedures. However, 3-6% of these are complicated by aortic or atrial perforations due to incorrect needle positioning. This relatively high complication rate can in part be attributed to the inability to directly visualize critical endocardial landmarks using a two-dimensional projection x-ray fluoroscopy. Conventional X-ray guided interventions suffer from a number of limitations, including: (1) limited anatomical visualization of the body and blood vessels during the examination, (2) limited ability to obtain a cross-sectional view of the target tissue or blood vessel, (3) inability to characterize important pathologic features of atherosclerotic plaques, (4) limited ability to obtain functional information on the state of the related organ, and (5) exposure of the subject to potentially damaging x-ray radiation.

Many invasive cardiovascular procedures, such as traversing total chronic vascular occlusions, would benefit from using MR guidance to accurately deliver interventional medical devices to target locations because MRI methods have fewer limitations than conventional X-ray techniques. For example, U.S. Pat. No. 6,606,513 to Lardo et al describes a method means for an MR trans-septal needle that can be visible on an MRI, can act as an antenna and receive MRI signals from surrounding subject matter to generate high-resolution images, and can enable real-time active needle tracking during MRI guided trans-septal puncture procedures. Interventional cardiology would also benefit from using MR guidance by exploiting MRI's excellent soft tissue contrast. For example, MRI is able to distinguish between infarcted and healthy myocardium to identify an appropriate location for stem cell delivery [1]. MRI is also able to distinguish between plaque and vessel walls [2-3] which facilitates traversing total chronic occlusions. Furthermore, recent research has demonstrated that a complete electrophysiologic study can now be performed entirely under MRI guidance, including the ability to navigate catheters and characterize the temporal and spatial formation of ventricular radiofrequency ablation lesions in vivo.

Additionally, MRI has been shown to guide mitral valvoplasty procedures. As these two therapies account for 95% of all trans-septal procedures performed, it is clear that the ability to perform safe trans-septal needle puncture under MRI guidance will be of great importance as the field of interventional cardiovascular MRI continues to evolve.

In order to perform such procedures under MR guidance, it is necessary to visualize a cardiac catheter and track it using MRI. Another key requirement in minimally-invasive or non-invasive procedures is to integrate the positioning of instruments, needles, or probes with image guidance to confirm that the trajectory or location is as safe as possible, and to provide images that enhance the ability of the physician to distinguish between tissue types. Placement may require acquisition of static images for planning purposes, either in a prior MRI examination or during the interventional MRI session, or real-time images in arbitrary scan planes during the positioning process. (Daniel et al. SMRM Abstr. 1997; 1928; Bornert et al. SMRM Abstr. 1997; 1925; Dumoulin et al. Mag Reson Med 1993; 29: 411-415; Ackerman et al. SMRM Abstr 1986; 1131; Coutts et al., Magnetic Resonance in Medicine 1998, 40:908-13).

Despite the several distinct advantages MRI has over x-ray fluoroscopy, MRI guided positioning of catheters and other devices has numerous challenges related to imaging artifacts, electromagnetic interference, and the necessity for cardiac and respiratory gating and rapid imaging and display. The invention described herein describes a procedure and required hardware to perform MR guided procedures with active tracking of the tip of the interventional device. Such a procedure may improve imaging applications in a number of interventional MRI guided therapies.

Device tracking techniques using MRI can generally be separated into passive and active tracking methods. Passive tracking is based on device visualization due to magnetic susceptibility artifacts. Magnetic susceptibility is a quantitative measure of a material's tendency to interact with and distort an applied magnetic field. Magnetic susceptibility artifacts are generated by inhomogeneities in the magnetic field due to a material with a magnetic susceptibility different than that of tissue [3-6]. Initial attempts to position and visualize endovascular devices in MR imaging were based on passive susceptibility artifacts produced by the device when exposed to the MR field.

U.S. Pat. No. 4,827,931, to Longmore and U.S. Pat. Nos. 5,154,179 and 4,989,608 to Ratner disclose the incorporation of paramagnetic material into endovascular devices to make the devices visible based on magnetic susceptibility imaging. U.S. Pat. No. 5,211,166 to Sepponen similarly discloses the use of surface impregnation of various "relaxants", including paramagnetic materials and nitrogen radicals, onto surgical instruments to enable their MR identification. However, these patents do not provide for artifact-free MR visibility in the presence of rapidly alternating magnetic fields, such as would be produced during echo-planar MR imaging pulse sequences used in real-time MR guidance of intracranial drug delivery procedures. Nor do these patents teach a method for monitoring with MR-visible catheters the outcomes of therapeutic interventions, such as, for example, drug delivery into brain tissues or cerebral ventricles.

Ultrafast imaging sequences generally have significantly lower spatial resolution than conventional spin-echo sequences. Image distortion may include general signal loss, regional signal loss, general signal enhancement, regional signal enhancement, and increased background noise. The magnetic susceptibility artifact produced by the device should be small enough not to obscure surrounding anatomy, or mask low-threshold physiological events that have an MR signature, and thereby compromise the physician's ability to perform the intervention. These relationships will be in part dependent upon the combined or comparative properties of the device, the particular drug, and the surrounding environment (e.g., tissue). No additional processing or hardware is required with passive tracking techniques. However, an additional limitation with passive tracking is that quantitative information about the catheter position or orientation is not obtained. This inhibits automatic scan plane prescription and the catheter must be manually kept within the scan plane.

U.S. Pat. No. 5,470,307 to Lindall discloses a low-profile catheter system with an exposed MR-visible coating containing a therapeutic drug agent, which can be selectively released at remote tissue sites by activation of a photosensitive chemical linker. However, in common with other currently used endovascular access devices, such as catheters, microcatheters, and guidewires, the catheter tip is difficult to see on MRI because of inadequate contrast with respect to surrounding tissues and structures. This makes accurate localization difficult and degrades the quality of the diagnostic information obtained from the image. Also, the mere observation of the location of the catheter in the drug delivery system does not reliably or consistently identify the position, movement and/or efficient delivery of drugs provided through the system. Thus, one objective of this invention is to provide for an MR-compatible and visible device that significantly improves the efficacy and safety of drug delivery at various tissue locations using MR guidance.

An improved method for passive MR visualization of implantable medical devices is disclosed in U.S. Pat. No. 5,782,764 to Werne. This invention minimizes MR susceptibility artifacts and controls eddy currents in the electromagnetic scattering environment, so that a bright "halo" artifact is created to outline the device in its approximately true size, shape, and position. In the method of the invention disclosed by Werne, an ultra thin coating of conductive material comprising 1-10% of the theoretical skin depth of the material being imaged is applied, wherein the susceptibility artifact due to the metal is negligible due to the low material mass. At the same time, the eddy currents are limited due to the ultra-thin conductor coating on the device.

A similar method employing a nitinol wire with Teflon coat in combination with extremely thin wires of a stainless steel alloy included between the nitinol wire and Teflon coat, has been reported in the medical literature by Frahm et al., Proc. ISMRM, 3, 1997, p. 1931.

Active catheter tracking requires the reception of the MR signal by the catheter through a receive coil located on a device that is coupled via a cable to the input port of an MR scanner. Henceforth, a receive coil located on a device and coupled via a cable to the scanner will be referred to as a microcoil. Most active tracking techniques project the magnitude sensitivity pattern of small microcoils located on the catheter onto three orthogonal axes. The location of the micro-coils can then be determined by identifying the peaks of the projections [7-9].

There is, however, a weakness with this approach in that the peaks of the projections do not necessarily correspond to the center of the micro-coil. The magnitude sensitivity profile of a coil also changes with different coil orientations. This makes peak finding through curve fitting difficult. The method is also inherently susceptible to noise; high-resolution scans are needed; and it is not possible to obtain orientation information from the magnitude projections of a single coil [10].

Exemplary of methods for active MR visualization of interventional medical devices is U.S. Pat. No. 5,211,165 to Dumoulin et al., which discloses an MR tracking and localizing system for a catheter based on transmit/receive microcoils positioned near the end of the catheter. Applications of such catheter-based devices in endovascular and endoscopic imaging have been described in the medical literature, for example, Hurst et al., Mag. Res. Med., 24, 1992, pp. 343-357, Kantor et al., Circ. Res., 55, 1984, pp. 55-60; Kandarpa et al., Radiology, 181, 1991, pp. 99; Bomert et al., Proc. ISMRM, 3, 1997, p. 1925; Coutts et al., Proc. ISMRM, 3, 1997, p. 1924; Wendt et al., Proc, ISMRM, 3, 1997, p. 1926; Langsaeter et al., Proc. ISMRM, 3, 1997, p. 1929; Zimmerman et al., Proc. ISMRM, 3, 1997, p. 1930; and, Ladd et al., Proc. ISMRM, 3, 1997, p. 1937.

Various imaging coils for interventional MRI are known in the art. U.S. Pat. No. 5,738,632 to Karasawa discloses an endoscope/rigidoscope with MRI coils located in the distal section of the device. U.S. Pat. No. 5,699,801 to Atalar et al describes a loop antenna for interventional MRI and spectroscopy applications. U.S. Pat. No. 5,348,010 to Schnall et al. discloses an inflatable MRI receiver coil employing a balloon.

U.S. Pat. No. 5,271,400 describes a tracking system for the position and orientation of an invasive device within a patient, wherein the device includes a receiver coil and an MR active sample. The receiver picks up magnetic resonance signals generated by the sample. The frequencies are proportional to the location of the coil along the applied field gradients, since the signals are received in the presence of these magnetic field gradients. The system is designed to enable location of the invasive device and enhanced imaging of a region around the invasive device.

U.S. Pat. Nos. 6,587,706 and 6,560,475 to Viswanathan disclose microcoils which can be used in medical devices to enhance RF response signals and to create fields to enhance imaging capability in MRI imaging systems. The microcoil design includes at least one pair of radially opposed microcoils, each microcoil having an outside microcoil diameter of 6 mm or less, individual windings of each microcoil together defining a geometric plane for each microcoil, and the plane of each microcoil being parallel to the plane of another microcoil in the pair of radially opposed microcoils.

U.S. Pat. No. 6,549,800 to Atalar et al discloses methods for in vivo magnetic resonance imaging, wherein MRI probes are adapted for insertion into a plurality of body orifices in order to evaluate the anatomy of proximate anatomic structures, to diagnose abnormalities thereof and to treat the diagnosed abnormalities. MRI probes are described that are suitable for use in the mediastinum, in the pancreaticohepaticobiliary system, in the tracheobronchopulmonary system, in the head and neck, in the genitourinary system, the gastrointestinal system, the vascular system, and in the evaluation, diagnosis and treatment of internal fluid collections.

U.S. Pat. No. 6,061,587 to Kucharczyk et al. discloses an apparatus and method for targeted drug delivery into a living patient using catheter-based microcoils and magnetic resonance (MR) imaging. The apparatus and method uses MRI to track the location of drug delivery and estimating the rate of drug delivery.

A different approach for remote sensing of location is disclosed by U.S. Pat. No. 5,042,486 to Pfeiler et al. and by U.S. Pat. No. 5,391,199 to Ben Haim. These technologies are based on generating weak radio-frequency signals from three different transmitters, receiving the signals through an RF antenna inside the device, and calculating the distances from the transmitters, which define the spatial location of the device. However, the application of this technology to MRI is problematic due to the simultaneous use of RF signals by the MR scanning. Potential difficulties are the heating of the receiving antenna in the device by the high amplitude excitation RF transmissions of the MRI scanner and artifacts in the MR image.

U.S. Pat. Nos. 5,271,400 and 5,211,165 to Dumoulin et al. disclose a tracking system employing magnetic resonance signals to monitor the position (since mentioned below that orientation information is not available) of a device within a human body. The device disclosed by Dumoulin's inventions have an MR-active sample and a receiver coil which is sensitive to MR signals generated by the MR-active sample. These signals are detected in the presence of MR field gradients and thus have frequencies which are substantially proportional to the location of the coil along the direction of the applied gradient. Signals are detected by sequentially applied, mutually orthogonal magnetic gradients to determine the device's position in several dimensions. The position of the device as determined by the tracking system is superimposed upon independently acquired medical diagnostic images. However, this method cannot directly determine the orientation of the device, may be subject to heating of the coil, and requires time to implement that reduces the temporal resolution available for repeated MRI acquisitions.

Although the patented inventions referenced above provide useful technological advances in the field of image-guided interventions, each invention also has significant inherent limitations. Unlike the present invention, which is based on phase information, the prior art references are based on magnitude information. Phase information can track an interventional device more accurately than magnitude sensitivity information because phase information is more spatially varying than magnitude projections. The present invention also provides notable advantages over the prior art by enabling the position and orientation of a catheter tip to be reliably tracked using low resolution MR scans for real-time interventional MRI applications. The prior art methods are also inherently susceptible to noise; high-resolution scans are needed; and it is not possible to obtain orientation information from the magnitude projections of a single coil [10].

SUMMARY OF THE INVENTION

One object of this invention is to provide a phase sensitivity method for tracking the position of endovascular access devices and interventional probes which is more accurate than magnitude sensitivity methods disclosed in the prior art.

A second object of the present invention is to provide a phase sensitivity method for reliably tracking the position of catheters using low-resolution clinically acceptable MRI scans that enable real-time interventional MRI applications.

A third object of this invention is to provide a phase sensitivity method which enables real-time MRI tracking of the position of endovascular access devices and interventional probes, including surgical tools and tissue manipulators, devices for in vivo delivery of drugs, angioplasty devices, biopsy and sampling devices, devices for delivery of RF, thermal, microwave or laser energy or ionizing radiation, and internal illumination and imaging devices, such as catheters, endoscopes, laparoscopes, electrophysiology electrodes and related instruments.

The present invention discloses a method for determining the position and/or orientation of a catheter or other interventional access device or surgical probe using phase patterns in a magnetic resonance (MR) signal. In the method of the invention, the position and orientation of a microcoil at the distal tip of the interventional device is established from the receive phase pattern of the microcoil, wherein an axial projection image of the microcoil's sensitivity pattern is initially created. The position of the microcoil in the axial plane is determined based on lines of constant phase which extend in the radial direction from the microcoil's edges, and the roll angle $\theta$ of the microcoil about the static magnetic field is established from the angle at which the phase pattern is rotated with respect to a reference axial phase pattern. Further in the method of the invention, an oblique slice is prescribed through the center of the microcoil and perpendicular to the plane in which the microcoil lies. According to the invention, the microcoil is then located in a third orthogonal direction based on discontinuities in the oblique phase pattern which extend radially from the microcoil's edges.

The pitch angle $\phi$ of the coil about a vector perpendicular to the oblique plane is determined by calculating the angle at which the oblique phase pattern is rotated with respect to a reference phase pattern. In the method of the invention, the phase in the two regions is then sampled to verify the calculation of the roll angle $\theta$ wherein the roll angle $\theta$ and the pitch angle $\phi$ form two Euler angles that can be used to determine the normal of the microcoil.

According to the invention, phase information can track the position of a catheter or other interventional device more accurately than magnitude sensitivity information because the receive phase sensitivity of a microcoil is unique for any given position and orientation of the microcoil, and phase information is more spatially varying than magnitude projections. In the method of the invention, both the position and orientation of a microcoil can be determined using phase information. Catheter tip tracking is carried out by obtaining two phase images; one integrated phase image projected onto the axial plane and one in an oblique plane through the center of the coil and normal to the microcoil plane. In another preferred embodiment of the invention, phase information adequate for MRI localization can also be obtained from only one plane, for example, a plane through the microcoil perpendicular to the axial plane, wherein such phase information is used together with position information obtained from projections, or based on a locator that produces substantial phase patterns. Furthermore, the phase images obtained for catheter tracking using the method of the present invention can be low-resolution MR images, wherein clinically useful MRI scans can be obtained relatively rapidly thereby making catheter tracking using phase information clinically useful for real-time interventional MRI applications.

In one aspect of the present invention there is provided a method of determining one or both of position and orientation of a medical device in a patient's body, the method comprising the steps of:

a) placing the medical device in a patient's body and placing the patient in a magnetic resonance imaging scanner, the magnetic resonance imaging scanner having means for producing magnetic resonance signals having a phase and magnitude and detection means for detecting magnetic resonance signals, and the medical device including at least one marker for perturbing the phase of the magnetic resonance signal;

b) acquiring magnetic resonance signals with perturbed phase from the patient's body using the detection means; and c) reconstructing from the acquired magnetic resonance signals with perturbed phase at least one map oVa spatial distribution of the phase of the received signals, and using selected characteristics of the spatial distribution of the phase to determine one or both of the device position and orientation of the medical device in the patient's body.

In another aspect of the present invention there is provided a method for determining the position and orientation of a medical device inserted into a body of a patient, comprising the steps of:

placing a medical device in a patient's body and placing the patient in a magnetic resonance imaging scanner, the magnetic resonance imaging scanner having means for producing magnetic resonance signals each having a phase and magnitude and detection means for detecting magnetic resonance signals;

the medical device including at least one marker for perturbing the phase of the magnetic resonance signals, the at least one marker including a microcoil;

detecting phase images with perturbed phase in magnetic resonance (MR) signals received by the microcoil;

determining the position and orientation of the medical device in the patient's body by producing an axial projection image of the at least one microcoil's integrated phase image in an axial plane, determining a position of the at least one microcoil in the axial plane based on lines of constant phase which extend in a radial direction from the at least one microcoil's edges, determining a roll angle $\theta$ of the at least one microcoil from an angle at which the phase image is rotated with respect to a reference axial phase image, prescribing an oblique slice, perpendicular to the axial plane, through a center of the at least one microcoil and perpendicular to the plane in which the at least one microcoil lies and then determining a location of the microcoil in a third orthogonal direction by noting that discontinuities in an oblique phase image extend radially from the at least one microcoil's edges, determining a pitch angle $\phi$ by calculating an angle at which the oblique phase image is rotated with respect to a reference phase image; and determining a normal of the at least one microcoil wherein the roll angle $\theta$ and the pitch angle $\phi$ form two Euler angles used to determine the normal of the at least one microcoil.

The present invention also provides an apparatus for determining one or both of position and orientation of a medical device in a patient's body, comprising:

a) medical device for insertion into a patient's body, the medical device including at least one marker for perturbing a phase of magnetic resonance signals;

b) a magnetic resonance imaging scanner, the magnetic resonance imaging scanner having means for producing said magnetic resonance signals each having said phase and a magnitude and detection means for detecting magnetic resonance signals responsively emitted from the patient's body; and c) the magnetic resonance imaging scanner including processing means for reconstructing from the detected magnetic resonance signals having perturbed phase at least one map of a spatial distribution of the phase of the detected signals, and using selected characteristics of the spatial distribution of the phase to determine one or both of the position and orientation of the medical device in the patient's body.

A further understanding of the functional and advantageous aspects of the invention can be realized by reference to the following detailed description and drawings.

BRIEF DESCRIPTION OF THE FIGURES

The catheter tracking with phase information produced according to the present invention will now be described, by way of example only, reference being made to the accompanying drawings, in which:

FIGS. 1a-d depicts various properties of phase patterns in the axial plane. The orientation of the micro coil is depicted with respect to a coordinate system (Left), the scan plane is depicted with respect to the microcoil (Middle), and the simulated phase image that corresponds to the plane are shown (Right).

FIGS. 2a-c depicts various properties of phase patterns in an oblique plane perpendicular to the axial plane through the center of the microcoil. The orientation of the micro coil is depicted with respect to a coordinate system (Left), the scan plane is depicted with respect to the microcoil (Middle), and the simulated phase image that corresponds to the plane are shown (Right).

FIG. 2a shows a simulated phase image in an oblique plane through the center of the microcoil.

FIG. 3a-c shows a graphical demonstration of a potential localization scheme in one embodiment of the invention.

FIGS. 4a-d shows a comparison between actual and simulated phase images obtained from a 4-mm-outside diameter microcoil at the tip of a 6F angiographic catheter positioned in an agar phantom using the method of the present invention. The phase images were acquired with a spin-echo imaging pulse sequence.

FIG. 4b shows a simulated projection phase image in the axial plane.

FIGS. 5a-d shows a comparison between actual and simulated phase images obtained from a 4-mm-outside diameter microcoil at the tip of a 6F angiographic catheter positioned in an agar phantom using the method of the present invention. The phase images were acquired using a spiral acquisition.

FIGS. 7a-b illustrates one possible application of the invention involving the guidance of a catheter through a chronic total occlusion.

DETAILED DESCRIPTION OF THE INVENTION

Definitions:

As used herein the phrase "phase pattern" refers to a spatial map of phase in the MR signal in a particular plane of interest.

As used herein the phrase "catheter tracking" refers to the act of determining information about the position and/or orientation of a catheter tip.

As used herein the phrase "marker for perturbing the phase of the magnetic resonance signal" means using a receive coil of arbitrary shape used to introduce phase into the MR signal through its receive sensitivity field or using a material of arbitrary shape and sufficient magnetic susceptibility to perturb the static magnetic field in the volume surrounding the material.

As used herein the phrase "microcoil" refers to small tuned radiofrequency antenna used to receive MR signal or transmit an MR excitation field.

As used herein the phrase "field map" refers to a spatial map of the static magnetic field in a plane of interest.

Active MRI tracking of catheters and other interventional probes has been a subject of research for more than a decade, but most studies have focused on magnitude sensitivity methods for localizing such devices. The fundamental weakness with this approach is that it produces inaccurate localization when the peak of the magnitude projections does not correspond to the location of the center of the microcoil. The magnitude sensitivity profile of the coil also changes with different coil orientations. The magnitude projection method is also inheritably susceptible to noise, high-resolution projections are needed, and orientation information cannot be obtained from projections alone.

The present invention addresses these various limitations of magnitude sensitivity methods by providing a novel method for determining the position and orientation of interventional access devices and surgical probes based on phase patterns in the MR signal around a marker positioned on the device or probe. More particularly, the present invention provides a method of determining the position and/or orientation of a medical device in a patient's body which involves placing the medical device in a patient's body and placing the patient in a magnetic resonance imaging (MRI) scanner. The medical device includes at least one marker for perturbing the phase of the magnetic resonance signal which is measured by the MRI scanner. Based on the received magnetic resonance signals acquired from the patient's body using the magnetic resonance imaging scanner, at least one map of the spatial distribution of the phase of the received signals is reconstructed, and using characteristics of the spatial distribution of the phase, the device position and/or orientation are determined.

In a preferred embodiment of the invention the marker is a small circular microcoil positioned on the device or probe. In this embodiment, the microcoil is used to acquire the MR signal. However, it will be appreciated that the microcoil does not need to be circular, it may for example be elliptical or square, and in addition any other type of marker may be used so long as it perturbs the phase of the magnetic resonance signal, for instance through any type of susceptibility mechanism. In this latter case, the marker is selected so that the difference in magnetic susceptibility between the marker and adjacent water in the body yields unique phase patterns in the signal around the marker which can be mapped using the MR signal received by an external coil.

Another example includes the introduction of a small piece of ferromagnetic material onto the probe which disrupts the local magnetic field. In this embodiment, MR signals can be acquired using an MR reception coil located external to the body. A further example is the introduction of a small bubble of carbon dioxide in a balloon attached to the device. Again, the difference in magnetic susceptibility between the gaseous carbon dioxide and adjacent water in the body yields unique phase patterns in the signal around the balloon which can be mapped using the MR signal received by an external coil.

When using a small circular microcoil positioned on the device or probe the method of the present invention determines the position and orientation of interventional access devices and surgical probes based on phase patterns in the MR signal around the small circular microcoil positioned on the device or probe.

The microcoil may be connected electrically to the MR system or signals from the coil may be coupled optically or inductively to a transducer which is electrically connected to the MR scanner. The latter embodiments provide some electrical isolation between the patient and the scanner. One can configure the system so that it is possible to separately receive signals from different coils at the same time. That said, when using microcoils, phase images are derived from the signal from each microcoil.

In the method of the invention, accurate position and orientation information can be obtained over a circular area of at least 4 microcoil diameters. Moreover, since only a sample of the information is needed to position and orient the catheter, highly redundant localization information is available and global correlations can be used to identify the phase patterns.

The present invention will now be described further with particular reference to certain non-limiting embodiments and to the accompanying drawings in FIGS. 1 to 4. In the method of the invention, the sensitivity field of a circular microcoil is evaluated. The theory of reciprocity states that the sensitivity field of an MR receive coil is equivalent to the magnetic field produced when current I is passed through the coil. The receive sensitivity of a circular receive coil can be described in cylindrical coordinates by the following equations:

$$B_{z'} = \frac{\mu I k}{4\pi\sqrt{ar}}\left[K(k) + \frac{a^2 - r^2 - z'^2}{(a-r)^2 + z'^2}E(k)\right] \quad [1]$$

$$B_r = \frac{\mu I k z'}{4\pi r\sqrt{ar}}\left[-K(k) + \frac{a^2 + r^2 + z'^2}{(a-r)^2 + z'^2}E(k)\right] \text{ where} \quad [2]$$

$$k = \sqrt{\frac{4ar}{(a-r)^2 + z'^2}}, \quad [3]$$

a is the coil's radius, μ is the magnetic permeability of the medium surrounding the coil, r is radial distance from the centre of the coil and z' is distance in the perpendicular direction. K(k) and E(k) are elliptic integrals of the first and second kind respectively. The directional component of the sensitivity introduces spatially varying phase patterns into the MR signal that are dependent solely on the position and orientation of the coil within the magnetic field. Assuming constant phase in the MR signal in the absence of the receive coil, the phase distribution introduced by the receive coil can be identified through a phase reconstruction of an image acquired from the receive coil.

Figure 1A:
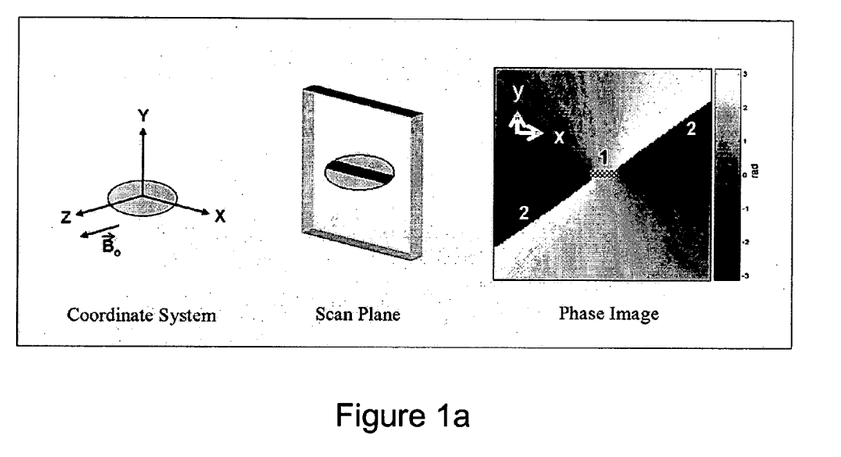
FIG. 1a shows a simulated phase image in the axial plane through the center of the microcoil.
Figure 1B:
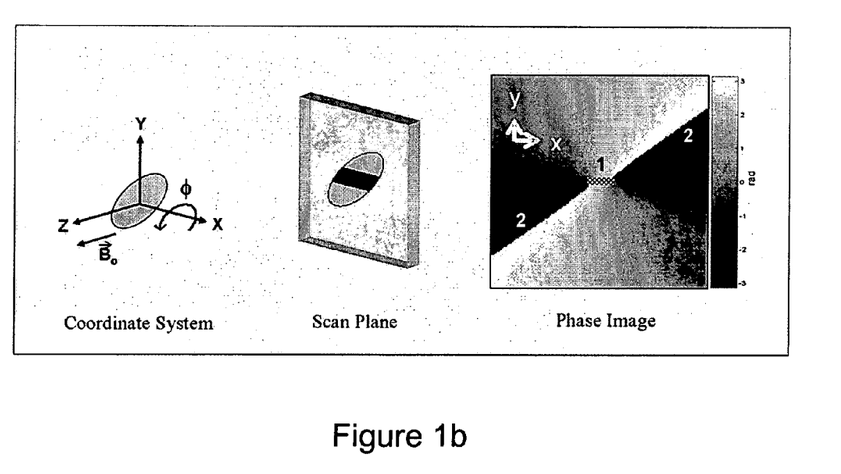
FIG. 1b shows a simulated phase image in the axial plane with the microcoil rotated by angle $\phi$ about the x-axis.
Figure 1C:
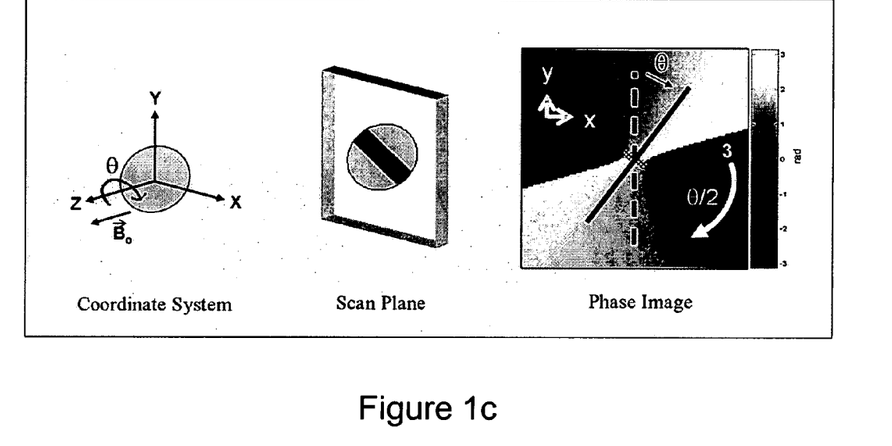
FIG. 1c shows a simulated phase image in the axial plane with the microcoil rotated by angle $\phi$ about the x-axis and by angle $\theta$ about the z-axis.
Figure 1D:
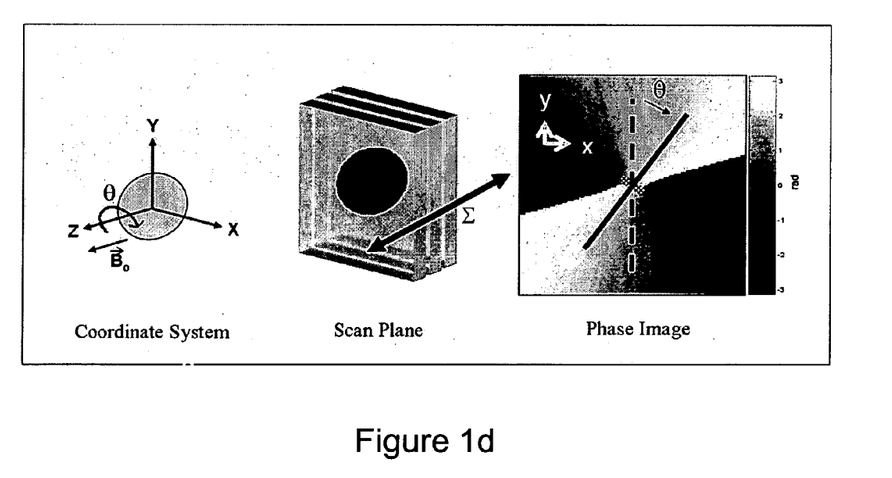
FIG. 1d shows a simulated projected phase image in the axial plane with the microcoil rotated by angle $\phi$ about the x-axis and by angle $\theta$ about the z-axis.
Figure 2A:
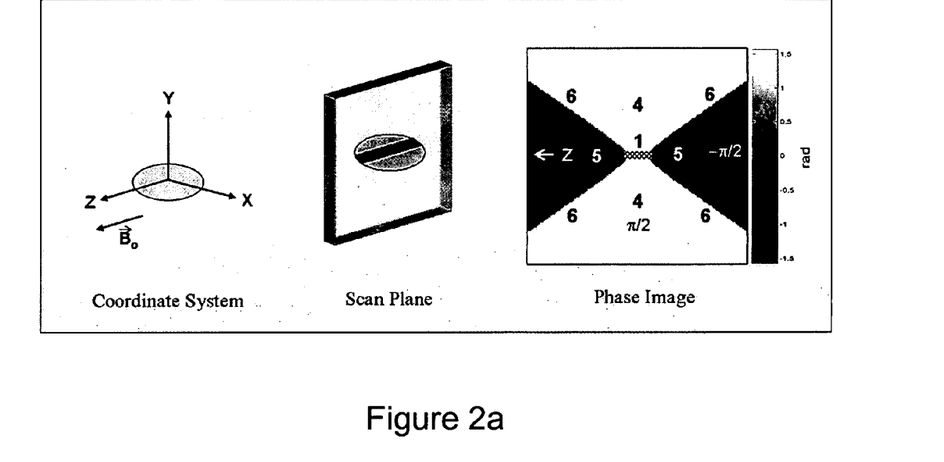
Figure 2B:
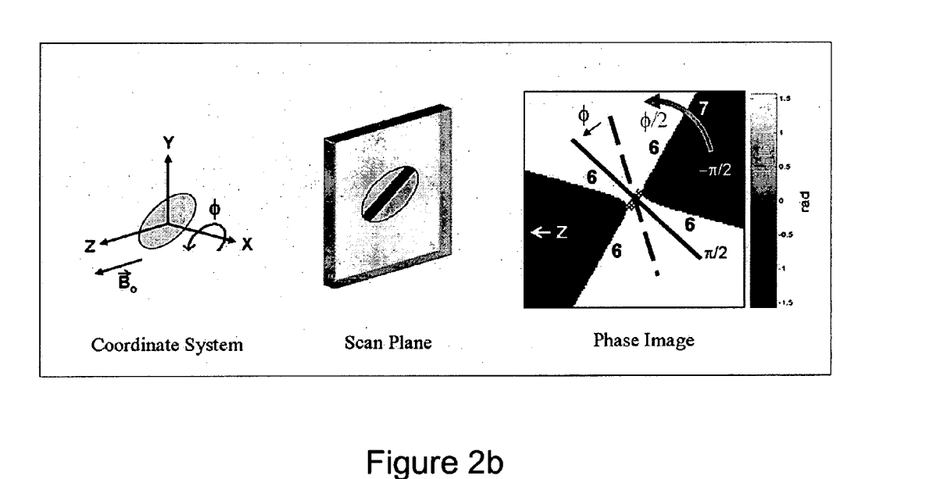
FIG. 2b shows a simulated phase image in an oblique plane through the center of the microcoil with the microcoil rotated by angle $\phi$ about a vector perpendicular to the oblique plane.
Figure 2C:
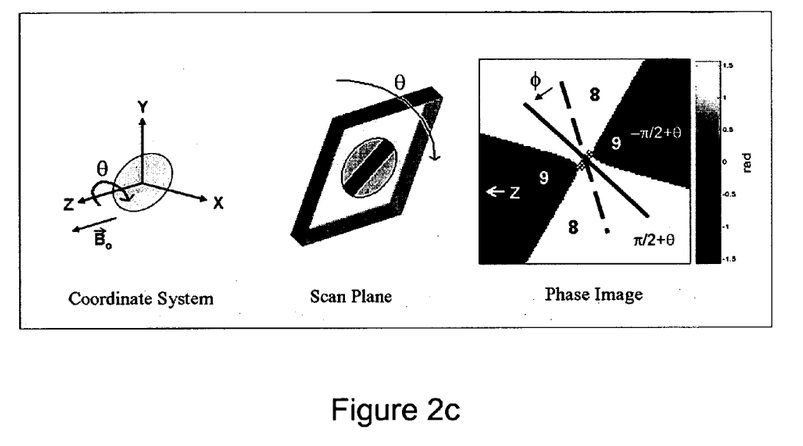
FIG. 2c shows a simulated phase image in an oblique plane through the center of the microcoil with the microcoil rotated by angle $\theta$ about the z-axis and rotated by angle $\phi$ about a vector perpendicular to the oblique plane.

With reference to FIG. 1a, when the radius of the microcoil is smaller compared to the field of view (FOV) (field of view being the size, in linear dimensions, of the acquired phase pattern), so that it satisfies the condition (a<FOV/10), the simulated magnetic field receive phase pattern around the circular microcoil 1 in the axial plane (perpendicular to the static field pointing along z) through the center of the coil has lines of constant phase extending in the radial direction from its edges 2. According to the invention, the phase pattern in the axial plane is independent of coil pitch about the x axis (magnet coordinate system) (FIG. 1b) and rotates by angle θ/2 3 with coil rotation about the z axis by angle θ (FIG. 1c), wherein this phase pattern is also independent of axial slice, wherein the same phase pattern results if the signal is integrated over the z-direction (magnet coordinate system) (FIG. 1d). Further in the method of the invention, the phase pattern in an oblique slice through the center of a micro coil lying in the z-x plane and normal to the coil plane (FIG. 2a) consists of two areas of constant phase, wherein the areas of constant phase have a value of π/2+θ above and below the coil and a value of −π/2+θ to the sides of the coil. The discontinuities 6 between the two areas extend in the radial direction from the coil edges. According to the invention, the phase pattern rotates by an angle φ/2 7 with coil rotation by angle φ about the direction normal to the oblique plane (FIG. 2b). With reference to FIG. 2c, when the coil is rolled by angle θ about the z axis, the values of phase in the two constant areas increase by θ to form a value of π/2+θ above and below the coil 8 and −π/2+θ to the sides of the coil 9.

Figure 3A:
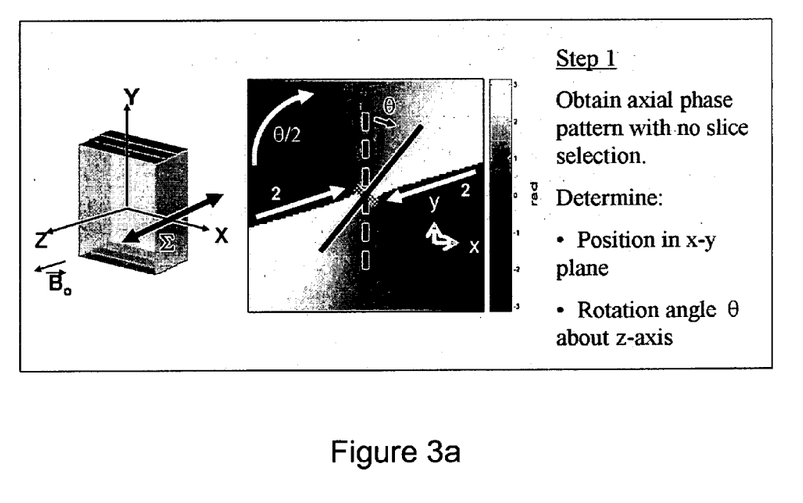
FIG. 3a shows a graphical demonstration of step 1 of a potential localization scheme in one embodiment of the invention. A projected phase image is obtained in the axial plane. The micro coil is positioned on the plane using the lines of constant phase as shown. The rotation of the coil $\theta$ about the z-axis is determined by measuring the rotation on the phase pattern with respect to a reference.
Figure 3B:
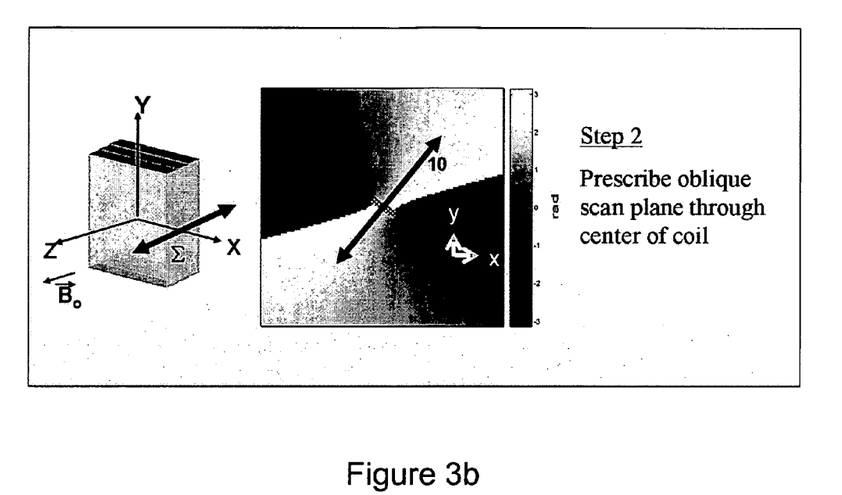
FIG. 3b shows step 2 of a potential localization scheme in one embodiment of the invention. An oblique plane perpendicular to the axial plane, passing through the center of the coil, and perpendicular to the plane in which the circular microcoil lies is prescribed.

With reference to FIG. 3, according to a preferred embodiment of the invention, the phase patterns around a circular microcoil can be used to determine the position and orientation of the microcoil. In the method of the invention, an axial projection image (no slice selection gradient) of the microcoil's sensitivity pattern is first created (FIG. 3a). In a preferred embodiment, the microcoil can be positioned on the x-y plane with reference to lines of constant phase which propagate radially from the edges of the microcoil. The amount θ by which the microcoil is rotated about the static field $B_o$ is determined by determining the amount by which the phase pattern is rolled. Further in the method of the invention, an oblique slice is then prescribed (drawn) through the center of the microcoil and perpendicular to the plane in which the microcoil lies 10 (FIG. 3b). Prescribing" means selecting an imaging plane, often done by drawing a line on an MR image to define a plane perpendicular to the current image passing through that line.

Figure 3C:
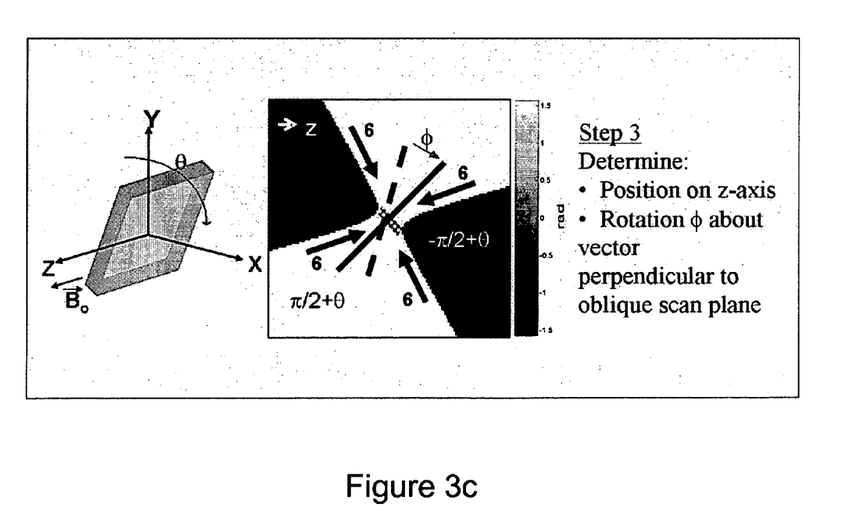
FIG. 3c shows step 3 of a potential localization scheme in one embodiment of the invention. Using the phase image corresponding to the oblique slice prescribed in FIG. 3b, the microcoil is positioned on the z-axis using discontinuities between regions of constant phase as show. The rotation of the coil $\phi$ about a vector perpendicular to the oblique plane is determined by measuring the rotation on the phase pattern with respect to a reference.

With reference to FIG. 3c, the microcoil can then be located on a third axis based on discontinuities in the oblique phase pattern 6 which extend radially from the microcoil's edges.

Further in the method of the invention, the pitch angle φ by which the coil is rotated about a vector perpendicular to the oblique plane, can be determined by calculating the angle at which oblique phase pattern is rotated with respect to a reference phase pattern. The phase in the two regions can then be sampled to verify the calculation of θ. The angles θ and φ form two Euler angles from which the microcoil's normal can be determined.

Figure 4A:
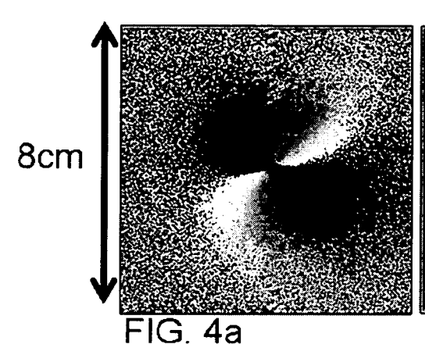
FIG. 4a shows a projection phase image acquired in the axial plane.
Figure 4C:
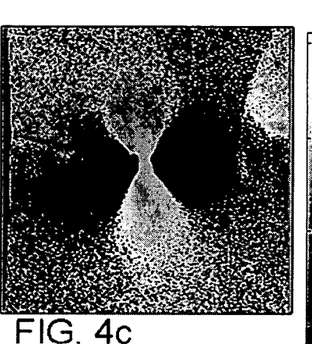
FIG. 4c shows a phase image acquired in the oblique plane.
Figure 4D:
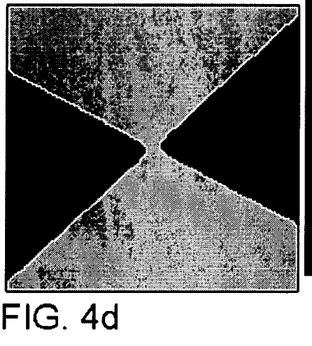
FIG. 4d shows a simulated phase image in the oblique plane.

In order to evaluate the utility of the present invention, a small microcoil with diameter 4-mm-outside diameter (30 gauge insulated magnet wire, 4 windings) was placed on the distal tip of a 6F angiographic catheter and embedded in an agar phantom. Phase patterns were obtained using a 1.5 T GE Signa CV/i MR scanner with a spin echo pulse sequence (FOV=8 cm, TE=17 ms, TR=5000 ms, 256×256). The phase patterns obtained from the microcoil are shown in FIGS. 4a and 4c with reference to simulated phase patterns around microcoils in a similar orientation. In the axial phase pattern obtained without slice selection (FIG. 4a) radial lines of constant phase extending from the coil's edges can clearly be seen, wherein the phase pattern resembles the simulations (FIG. 4b). The phase pattern in the oblique slice (FIG. 4c) consists of two regions of constant phase, wherein phase values in these regions are in agreement with the predicted values (FIG. 4d).

In another embodiment of the invention, phase inhomogeneities can be corrected for by obtaining two separate phase images at different echo times and generating a field map to perform post-acquisition corrections of static magnetic field inhomogeneities.

Figures 5, 5A, 5B, 5C, 5D:
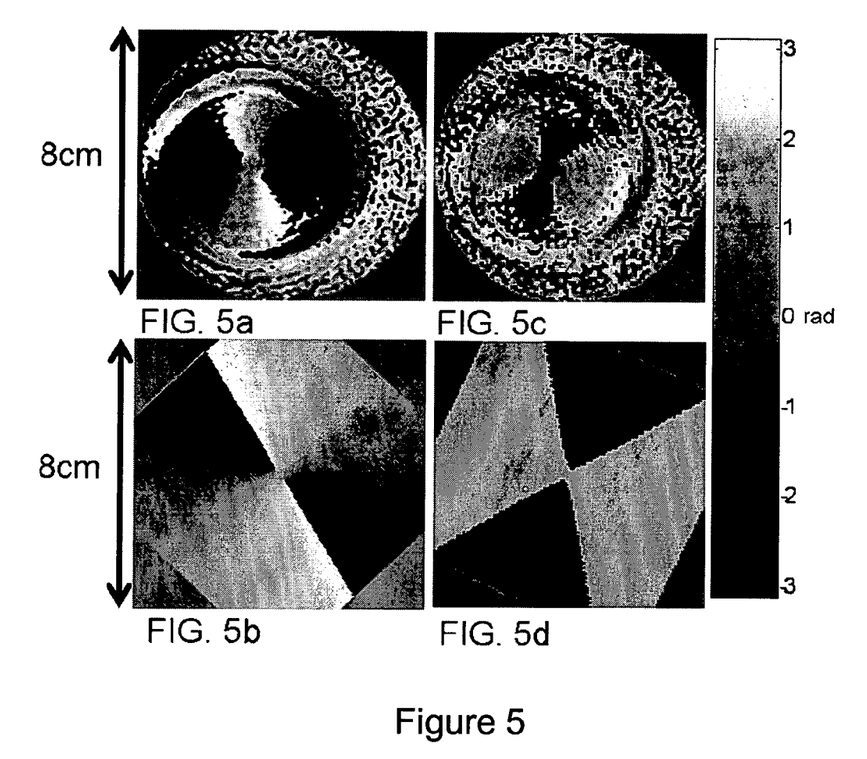
FIG. 5a shows a projection phase image acquired in the axial plane.
FIG. 5b shows a simulated projection phase image in the axial plane.
FIG. 5c shows a phase image acquired in the oblique plane.
FIG. 5d shows a simulated phase image in the oblique plane.

In another embodiment, the necessary phase images can be acquired rapidly using a fast acquisition technique. In this embodiment the methods for tracking the device are identical to previous embodiments with the exception that a rapid acquisition technique is used to collect the phase data in the planes described in FIGS. 3a-3c. In this embodiment, phase image quality is sacrificed for acquisition speed to enable tracking with a high temporal resolution. An example of a rapid imaging technique is spiral acquisition which collects data in a rapid and efficient manner. The utility of this embodiment was investigated by acquiring phase patterns in the planes of interest using the same microcoil discussed above using a spiral acquisition (FOV=8 cm, TR=36 ms, TE=10 ms, FA=45 deg, 3 4096-point spiral interleaves in k-space with an additional acquisition for field map calculation, total acquisition time=216 ms). The phase patterns obtained from the microcoil using a spiral acquisition are shown in FIGS. 5a and 5c with reference to simulated phase patterns around microcoils in a similar orientation. In the axial phase pattern obtained without slice selection (FIG. 5a) radial lines of constant phase extending from the coil's edges can clearly be seen, wherein the phase pattern resembles the simulations (FIG. 5b). The phase pattern in the oblique slice (FIG. 5c) consists of two regions of constant phase, wherein phase values in these regions are in agreement with the predicted values (FIG. 5d).

The results of the simulation studies underscore several advantages of the phase sensitivity method of the present invention. Unlike magnitude sensitivity methods disclosed in the prior art, phase patterns are unique to a microcoil's position and orientation and yield accurate information about both localization parameters. According to the present invention, phase pattern information also provides a more robust localization algorithm, since phase patterns are more spatially varying than magnitude projections and yield clear position and orientation information over a circular area of at least 4 coil diameters.

Furthermore, since global two-dimensional correlations can be used to identify the phase patterns, low-resolution scans may be sufficient for locating the coil. As a result, localization using the phase pattern methods disclosed by this invention may prove particularly useful in real-time applications, wherein as one non-limiting example, if the coil were to be located within a 2 cm volume, a single spiral acquisition at sufficient resolution (2 cm FOV, 1.05 mm resolution, 31.25 kHz bandwidth, 1024 readout) could be performed on a 1.5 T GE Signa CV/i system in 16 ms. According to this application of the method of the invention, catheter position and orientation could be determined in under 100 ms even with extra acquisitions to correct for inhomogeneities.

In another preferred embodiment of the present invention, active MR localization of the orientation and position of an interventional device may also be achieved by means of several microcoils positioned along the longitudinal axis of a catheter or other interventional device. Particularly preferred are microcoils consisting of a circular loop of conductive material positioned around the functional parts of an interventional device, such as a drug delivery catheter. Depending on the orientation of the coil with the magnetic $B_0$, single microcoils may be used separately or may be constructed in an array. In order to reduce the thickness of the microcoil, the coil material may be sputter-coated onto the surface of the device. To provide information about angular twist of the device, the loop may be sputter-coated onto the side of the device rather than in a plane perpendicular to the longitudinal axis of the device. Also preferred is a microcoil able to move and rotate inside a catheter sleeve attached to another component of the device. This could be used to provide position and/or orientation information about this component (eg. shaft) inside the catheter). In another preferred embodiment, more than one microcoil may be present, wherein the distribution of microcoils along a length of the catheter defines the MR-visible region of the interventional device. In general, this embodiment of the invention is best practiced by employing an array of microcoils, such that an MR image is obtained for any orientation of the interventional device.

According to the invention, where functional elements are combined into a single interventional device, the positioning and orientation of several microcoils may be tailored for a particular interventional procedure. In the method of the invention, one or more microcoils may be positioned near or at the distal end of the central catheter to assist in positioning the device at a target anatomical location. Other configurations of microcoils, such as parallel alignment of the microcoils in a strip-like orientation, stacking of microcoils in rows and columns, or mixtures of these and other configurations may also be useful in the practice of the present invention.

Figure 6:
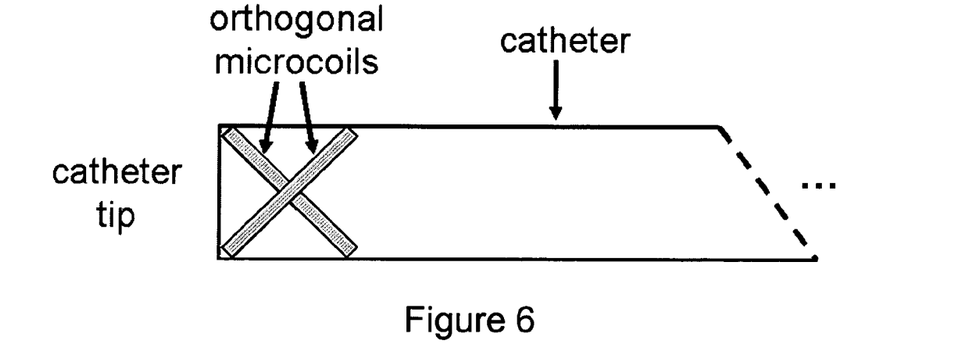
FIG. 6 shows an embodiment of the invention which uses two microcoils oriented perpendicularly to each other.

In another embodiment of the present invention, two microcoils are placed in orthogonal directions at the distal tip of the catheter, as shown in FIG. 6. In this configuration tracking is performed using both coils. Advantages with this configuration include the ability to track the device with adequate signal regardless of device orientation. In this configuration there is also minimal inductive coupling between microcoils. Furthermore, the configuration is well suited for acquiring high-resolution images of the anatomy immediately surrounding the device.

Other functional elements of interventional probes which may be localized using the method of the invention include thermal elements for providing heat, radiation carrying elements (e.g., ultraviolet radiation, visible radiation, infrared radiation), optical fibers, detection elements (e.g., pH indicators, electronic activity indicators, pressure detectors, ion detectors, thermal detectors, etc.), and any other sensing or detection element which would be useful during medical procedures. In accordance with the method of the invention, these individual elements would benefit from accurate directed placement of the functional tip of the device within the target site in a tissue. For example, in the treatment of neurological diseases and disorders, targeted drug delivery can significantly improve therapeutic efficacy while minimizing systemic side-effects of the drug therapy. Image-guided placement of the tip of a drug delivery catheter directly into specific regions of the brain can initially produce maximal drug concentration close to the loci of tissue receptors following injection of the drug. High-resolution visual images denoting the actual position of the drug delivery device within the brain are extremely useful to the clinician in maximizing the safety and efficacy of the procedure. In a particularly preferred embodiment, drug delivery devices, such as catheters, could be monitored by the MR phase tracking method of the present invention, thus making intra-operative verification of catheter location possible.

The present invention also overcomes other limitations of the prior art. For example, the limited distribution of drug injected from a single catheter location can reduce the therapeutic efficacy of the intervention in cases of anatomically extensive neurological damage, such as, for example, with certain brain tumors and stroke. Since the volume flow rate of drug delivery typically must be very low in order to avoid indiscriminate damage to brain cells and nerve fibers, delivery of a drug from a single point source limits the distribution of the drug by decreasing the effective radius of penetration of the drug agent into the surrounding tissue receptor population. Another aspect of this invention is therefore to overcome these inherent limitations of single point source drug delivery by devising a catheter tracking method which provides the ability for accurately monitoring the placement of a catheter tip at several tissue locations in order to allow multiple drug release sources, which effectively disperse therapeutic drug agents over a brain region containing receptors for the drug, or over an anatomically extensive area of brain pathology.

The availability of an MR-visible drug delivery device combined with clinically acceptable low-resolution imaging would make it possible to obtain near real-time information on drug delivery during interventional procedures in an intra-operative MR system, as well as for pre-operative and post-operative confirmation of the location of the drug delivery device. Medical and surgical applications of the present invention would include vascular surgery and interventional radiology, cardiac surgery and cardiology, thoracic surgery and radiology, gastrointestinal surgery and radiology, obstetrics, gynecology, urology, orthopedics, neurosurgery and neurointerventional radiology, head and neck surgery and radiology, ENT surgery and radiology, and oncology. In addition to direct tissue injection, the method of the invention applies to drug delivery via intraluminal, intracavitary, laparoscopic, endoscopic, intravenous, intraarterial applications.

Figure 7A:
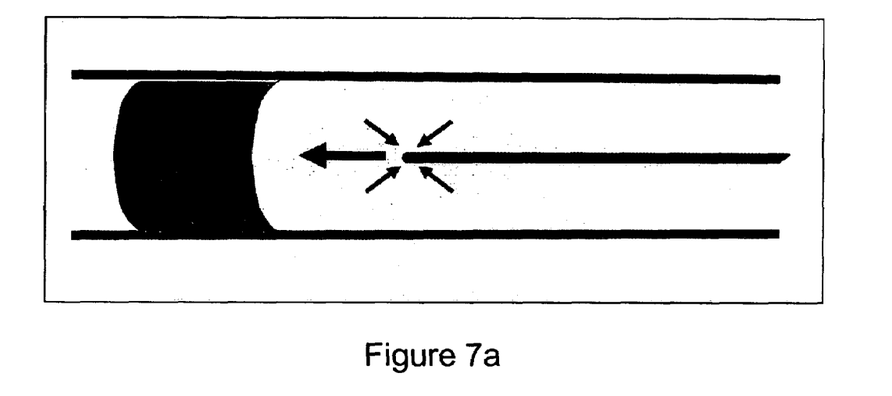
FIG. 7a graphically illustrates how position and orientation information about a catheter tip can be used to place a device in a blood vessel at the proximal end of an occlusion and parallel to the vessel wall.
Figure 7B:
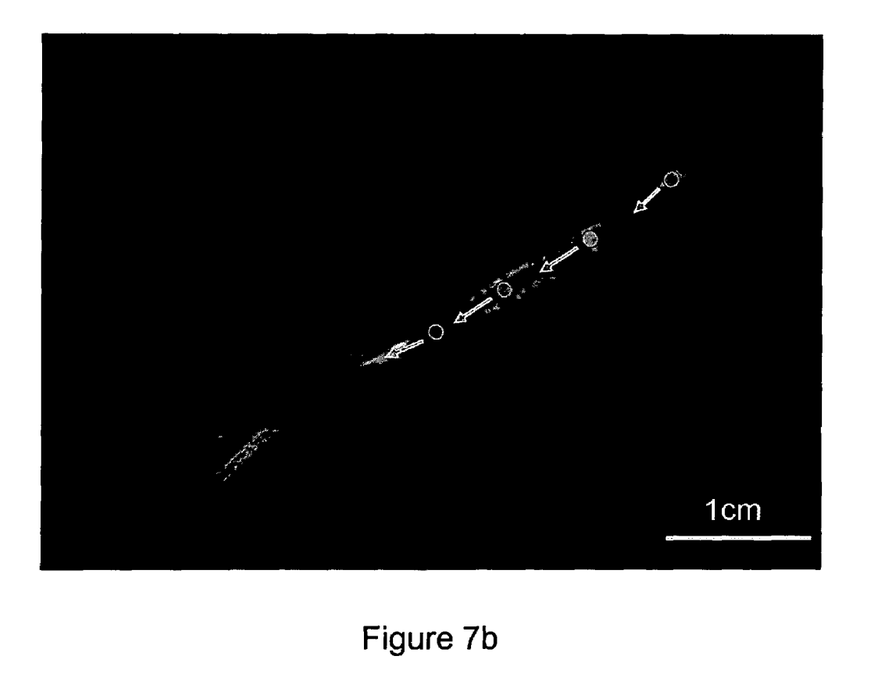
FIG. 7b shows one embodiment of the invention where phase information is used to provide position and orientation information about a catheter tip. The information is subsequently displayed on an MR image of a chronic total occlusion for guidance purposes.

The present invention also provides clinical benefits for certain cardiovascular procedures, such as, for example, traversing chronic total occlusions, where an intravascular device is pushed through a chronic occlusion in an artery to re-establish blood flow. Knowledge of the orientation and position of the device tip with respect to both the occlusion and vessel wall is extremely important because of significant risk of incidental surgical damage to the vessel wall (FIG. 7a). MRI can now reliably differentiate vessel wall from surrounding tissue. The method of the present invention can be used to determine and image both the position and orientation of a device with respect to critical anatomic landmarks resulting in improved safety and procedural efficacy. In a preferred embodiment, device position and orientation would be imaged in real-time on an MR image thereby providing clinically beneficial guidance for the procedure (FIG. 7b).

In a particularly preferred embodiment, the present invention can also be used for targeted delivery of stem cells in the myocardium. In order to achieve preferential migration of stem cells into infracted myocardium, injections must be made at the border between diseased and healthy tissue. MR can be used to identify such sites through delayed contrast-enhanced images, wherein the method of the present invention can be used to guide an injection device to appropriate target sites in the penumbra of the ischemic myocardium and to properly orient the injection needle for delivery of cells into region best suited for establishing functional improvement.

It should be understood that the foregoing description is merely illustrative of the invention. Various alternatives and modifications can be devised by those skilled in the art without departing from the scope or spirit of the invention. Accordingly, the present invention is intended to embrace all such alternatives, modifications and variances which fall within the scope of the appended claims.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES CITED

U.S. Patent Documents

| 4827931 | May, 1989 | Longmore | 128/334. |
|---|---|---|---|
| 4984573 | January, 1991 | Leunbach | 128/653. |
| 4989608 | February, 1991 | Ratner | 128/653. |
| 5154179 | October, 199 | Ratner | 128/653. |
| 5155435 | October, 1992 | Kaufman et al | 324/309. |
| 5188111 | February, 1993 | Yates et al. | 128/657. |
| 5201314 | April, 1993 | Bosley et al. | 128/662. |
| 5211166 | May, 1993 | Sepponen | 128/653. |
| 5218964 | June, 1993 | Sepponen | 128/653. |
| 5262727 | November, 1993 | Behbin et al. | 324/318. |

-continued

| 5271400 | December, 1993 | Dumoulin et al | 128/653. |
|---|---|---|---|
| 5290266 | March, 1994 | Rohling et al. | 604/272. |
| 5318025 | June, 1994 | Dumoulin et al. | 128/653. |
| 5353795 | October, 1994 | Souza et al. | 128/653. |
| 5357958 | October, 1994 | Kaufman | 128/653. |
| 5409003 | April, 1995 | Young | 128/653. |
| 5419325 | May, 1995 | Dumoulin et al. | 128/653. |
| 5534778 | July, 1996 | Loos et al. | 324/318. |

Other Documents

[1] Dick A J, Guttman M A, Raman V K, Peters D C, Pessanha B S, Hill J M, Smith S, Scott G, McVeigh E R, Lederman R J. "Magnetic resonance fluoroscopy allows targeted delivery of mesenchymal stem cells to infarct borders in Swine." Circulation 108(23): 2899-904.

[2] Barkhausen J, Ebert W, Heyer C, Debatin J F, Weinmann H J. "Detection of atherosclerotic plaque with Gadofluorine-enhanced magnetic resonance imaging." Circulation 108(5): 605-9.

[3] Wentzel J J, Aguiar S H, Fayad Z A. "Vascular MRI in the diagnosis and therapy of the high risk atherosclerotic plaque." J Interv Cardiol 16(2): 129-42.

[4] Glowinski A, Adam G, Bucker A, Neuerburg J, van Vaals J J, Gunther R W. "Catheter visualization using locally induced, actively controlled field inhomogeneities." Magn Reson Med 38(2): 253-8.

[5] Bakker C J G, Weber J, van Walls J J van, Mali W P T M, Viergever M A. "Dedicated Catheters for Susceptibility-Based MR Visualization." $4^{th}$ ISMRM, New York, 1996. Pg. 900.

[6] Lenz G, Drobnitzky M, Dewey Ch. "MR-visible catheters for intro-vascular interventional MRI procedures." $4^{th}$ ISMRM, New York, 1996. Pg. 901.

[7] Dumoulin C L, Souza S P, Darrow R D. "Real-time position monitoring of invasive devices using magnetic resonance." Magn Reson Med 29(3): 411-5.

[8] Elgort, D R, Wong E. Y, Hillenbrand C, Wacker F K, Lewin J S, Duerk, J L. "Real-time catheter tracking and adaptive imaging." J Magn Reson Imaging 18(5): 621-6.

[9] Santos J M, McConnell M, Scott G, Hyon M S, Pauly J M. "Multi-Coil Real-Time Interventional System." $11^{th}$ ISMRM, Toronto, 2003. 1197.

[10] Hillenbrand C M, Elgort D R, Wong E Y, Wacker F K, Lewing J S, Duerk J L. "A Catheter Based, Opposed Solenoid Phased Array Coil for Active Device Tracking and High Resolution Intravascular MRI." $11^{th}$ ISMRM, Toronto, 2003. 1186.

Therefore what is claimed is:

1. A method of determining one or both of position and orientation of a medical device in a patient's body, the method comprising the steps of:

a) placing the medical device in a patient's body and placing the patient in a magnetic resonance imaging scanner, the magnetic resonance imaging scanner having means for producing magnetic resonance signals having a phase and magnitude and detection means for detecting magnetic resonance signals, and the medical device including at least one marker for perturbing the phase of the magnetic resonance signals;

b) acquiring magnetic resonance signals with perturbed phase from the patient's body using the detection means; and c) reconstructing from the acquired magnetic resonance signals with perturbed phase at least one map of a spatial distribution of the phase of the received signals, and using selected characteristics of the spatial distribution of the phase to determine one or both of the device position and orientation of the medical device in the patient's body.

2. The method of claim 1 wherein the at least one marker is at least one microcoil, and wherein the at least one map of the spatial distribution of the phase comprise at least one image in an oblique plane through a center of the microcoil and normal to an axial plane, where the axial plane is defined as being perpendicular to a direction of a main static magnetic field of the magnetic resonance imaging scanner.

3. The method of claim 2 wherein the at least one map of the spatial distribution of the phase also comprises at least one integrated phase image projected onto the axial plane.

4. The method of claim 3 wherein step c) of reconstructing from the acquired magnetic resonance signals at least one map of the spatial distribution of the phase of the received signals includes
- determining a position of the microcoil in the axial plane based on lines of constant phase which extend in a radial direction from the microcoil's edges,
- determining a roll angle θ of the microcoil from an angle at which the integrated phase image is rotated with respect to a reference integrated phase image,
- prescribing an oblique slice, perpendicular to the axial plane, through a center of the microcoil and perpendicular to the plane in which the microcoil lies and then determining a location of the microcoil in a third orthogonal direction by noting that discontinuities in an oblique phase image extend radially from the microcoil's edges,
- determining a pitch angle φ by calculating an angle at which the oblique phase image is rotated with respect to a reference phase image; and
- determining a normal of the microcoil wherein the roll angle θ and the pitch angle φ from two Euler angles used to determine the normal of the microcoil.

5. The method of claim 2 wherein the magnetic resonance signals are acquired using a magnetic resonance reception coil located external to the patient's body.

6. The method of claim 1 wherein the magnetic resonance signals are acquired using a magnetic resonance reception coil located external to the patient's body.

7. The method of claim 1 wherein the at least one marker is connected electrically to the detection means of the magnetic resonance imaging scanner and magnetic resonance signals are electrically transmitted from the at least one marker to the detection means.

8. The method of claim 1 wherein in step (a) the magnetic resonance imaging scanner uses low resolution magnetic resonance scans clinically useful for real-time interventional magnetic resonance imaging applications.

9. The method of claim 1 including providing real-time computer control to track the position of the medical device, and wherein the medical device is any one of endovascular access devices and interventional treatment systems selected from the group consisting of surgical tools and tissue manipulators, devices for in vivo delivery of drugs, angioplasty devices, biopsy and sampling devices, devices for delivery of RF, thermal, microwave or laser energy or ionizing radiation, and internal illumination and imaging devices.

10. The method of claim 1 wherein the at least one marker is selected so that a difference in magnetic susceptibility between the at least one marker and adjacent water in the patient's body yields unique phase images in the magnetic resonance signals around the at least one marker which can be mapped using the magnetic resonance signals received by an external coil.

11. A method for determining the position and orientation of a medical device inserted into a body of a patient, comprising the steps of:
- placing a medical device in a patient's body and placing the patient in a magnetic resonance imaging scanner, the magnetic resonance imaging scanner having means for producing magnetic resonance signals each having a phase and magnitude and detection means for detecting magnetic resonance signals;
- the medical device including at least one marker for perturbing the phase of the magnetic resonance signals, the at least one marker including a microcoil;
- detecting phase images with perturbed phase in magnetic resonance (MR) signals received by the microcoil;
- determining the position and orientation of the medical device in the patient's body by producing an axial projection image of the at least one microcoil's integrated phase image in an axial plane, determining a position of the at least one microcoil in the axial plane based on lines of constant phase which extend in a radial direction from the at least one microcoil's edges,
- determining a roll angle θ of the at least one microcoil from an angle at which the phase image is rotated with respect to a reference axial phase image,
- prescribing an oblique slice, perpendicular to the axial plane, through a center of the at least one microcoil and perpendicular to the plane in which the at least one microcoil lies and then determining a location of the microcoil in a third orthogonal direction by noting that discontinuities in an oblique phase image extend radially from the at least one microcoil's edges,
- determining a pitch angle φ by calculating an angle at which the oblique phase image is rotated with respect to a reference phase image; and
- determining a normal of the at least one microcoil wherein the roll angle θ and the pitch angle φ form two Euler angles used to determine the normal of the at least one microcoil.

12. The method of claim 11 wherein the magnetic resonance signals are acquired using a magnetic resonance reception coil located external to the patient's body.

13. An apparatus for determining one or both of position and orientation of a medical device in a patient's body, comprising:
a) medical device for insertion into a patient's body, the medical device including at least one marker for perturbing a phase of magnetic resonance signals;
b) a magnetic resonance imaging scanner, the magnetic resonance imaging scanner having means for producing said magnetic resonance signals each having said phase and a magnitude and detection means for detecting magnetic resonance signals responsively emitted from the patient's body; and
c) the magnetic resonance imaging scanner including processing means for reconstructing from the detected magnetic resonance signals having perturbed phase at least one map of a spatial distribution of the phase of the detected signals, and using selected characteristics of the spatial distribution of the phase to determine one or both of the position and orientation of the medical device in the patient's body.

14. The apparatus of claim 13 wherein the at least one marker is selected so that a difference in magnetic susceptibility between the at least one marker and adjacent water in the patient's body yields unique phase images in the detected magnetic resonance signals around the at least one marker which can be mapped using the MR signal received by an external coil.

15. The apparatus of claim 13 wherein the at least one marker comprises at least one microcoil.

16. The apparatus of claim 15 wherein the at least one microcoil has a shape which is one of a circular, ellipsoidal and square.

17. The apparatus of claim 15 wherein the at least one microcoil has a radius a which satisfies a condition, a <FOV/10, where FOV is a field of view.

18. The apparatus of claim 15 wherein the medical device has a longitudinal axis, and wherein the at least one microcoil is a distribution of microcoils disposed along a length of the medical device, and wherein the distribution of microcoils along the length of the medical device defines an MR-visible region of the medical device such that an MR image is obtained for any orientation of the medical device.

19. The apparatus of claim 13 wherein the detection means includes a magnetic resonance reception coil.

20. The apparatus of claim 13 wherein the at least one marker is a microcoil, and wherein said microcoil is connected electrically to the detection means of the magnetic resonance imaging scanner and magnetic resonance signals are electrically transmitted from the at least one marker to the detection means.

21. The apparatus of claim 13 wherein the at least one marker is a microcoil, and wherein said microcoil is coupled optically or inductively to a transducer which is electrically connected to the detection means of the magnetic resonance imaging scanner.

22. The apparatus of claim 13 wherein the medical device has a tubular structure and has a longitudinal axis, and wherein the at least one marker is at least one microcoil, and wherein said microcoil extends about a circumference of the tubular structure in a plane perpendicular to the longitudinal axis of the medical device.

23. The apparatus of claim 13 wherein the at least one marker is attached to a side of the medical device.

24. The apparatus of claim 13 wherein the medical device has a longitudinal axis, and wherein the at least one marker is a plurality of microcoils disposed along the longitudinal axis of the medical device.

25. The apparatus of claim 13 wherein the medical device has a leading end portion for insertion into the patient's body, and wherein the at least one marker is attached to the medical device at the leading end portion thereof.

26. The apparatus of claim 13 wherein the at least one marker is at least two microcoils placed in orthogonal directions to each other.

27. The apparatus of claim 13 wherein the at least one marker is mounted on the medical device so that it can move and rotate inside a housing forming part of the medical device.

28. The apparatus of claim 13 wherein the at least one marker comprises at least one small piece of ferromagnetic material affixed to the medical device which disrupts a magnetic field in a local vicinity of the ferromagnetic material.

29. The apparatus of claim 13 wherein the at least one marker comprises a small bubble of an effective gas contained in a balloon attached to the medical device the effective gas being selected so that a difference in magnetic susceptibility between the effective gas and adjacent water in the patient's body yields unique phase images in the magnetic resonance signals around the balloon.

30. The apparatus of claim 29 wherein the effective gas is carbon dioxide.

31. The apparatus of claim 13 wherein the medical device is any one of a catheter, an endoscope, a laparoscope, and an electrophysiology electrode.

32. The apparatus of claim 13 wherein the medical device is any one of endovascular access devices and interventional treatment systems selected from the group consisting of surgical tools and tissue manipulators, devices for in vivo delivery of drugs, angioplasty devices, biopsy and sampling devices, devices for delivery of RF, thermal, microwave or laser energy or ionizing radiation, and internal illumination and imaging devices.

* * * * *